United States Patent
Hutchings et al.

(10) Patent No.: US 9,574,995 B2
(45) Date of Patent: Feb. 21, 2017

(54) CO2 CONCENTRATION SENSOR

(71) Applicant: WITHINGS, Issy les Moulineaux (FR)

(72) Inventors: Cédric Hutchings, Issy les Moulineaux (FR); Nadine Buard, Meudon (FR); David Campo, Paris (FR); Brice Brac de la Perriere, Paris (FR); Pierre Barrochin, Saint Cloud (FR); Xavier Debreuil, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 0 days.

(21) Appl. No.: 14/759,008

(22) PCT Filed: Dec. 30, 2013

(86) PCT No.: PCT/FR2013/053281
§ 371 (c)(1),
(2) Date: Jul. 2, 2015

(87) PCT Pub. No.: WO2014/106717
PCT Pub. Date: Jul. 10, 2014

(65) Prior Publication Data
US 2015/0338339 A1    Nov. 26, 2015

(30) Foreign Application Priority Data

Jan. 2, 2013  (FR) ..................... 13 50014

(51) Int. Cl.
*G01N 21/00*  (2006.01)
*G01N 21/3504* (2014.01)
(Continued)

(52) U.S. Cl.
CPC ..... *G01N 21/3504* (2013.01); *G01N 21/3103* (2013.01); *G01N 21/314* (2013.01);
(Continued)

(58) Field of Classification Search
CPC .......... G01N 21/3103; G01N 21/3151; G01N 21/3504; G01N 21/35; G01N 21/59; G01N 2021/3155; G01N 33/004; G01N 2201/061
(Continued)

(56) References Cited

U.S. PATENT DOCUMENTS 5,222,389 A * 6/1993 Wong ................... G01N 1/2258
                                                      250/338.5
5,341,214 A    8/1994 Wong
(Continued)

FOREIGN PATENT DOCUMENTS

EP    2 293 043 A2    3/2011

OTHER PUBLICATIONS

International Search Report Application No. PCT/FR2013//053281 report dated Mar. 5, 2014.

*Primary Examiner* — Hoa Pham
(74) *Attorney, Agent, or Firm* — Miller, Matthias & Hull LLP

(57) ABSTRACT

Device for measuring the concentration of a predetermined gas, in particular CO2, comprising a cavity, a light source emitting light rays within a basic spectral range including visible and infrared, a detector configured to receive a portion of the light rays within a first predefined spectral range corresponding to high absorption of the predetermined gas, a photodiode configured to receive a portion of the light rays within a second predefined spectral range corresponding to low absorption of the predetermined gas, a control unit configured to calculate the concentration of the predetermined gas by comparing the radiant power received by the detector to the radiant power received by the photodiode.

11 Claims, 2 Drawing Sheets

(51) Int. Cl.
*G01N 21/31* (2006.01)
*G01N 33/00* (2006.01)

(52) U.S. Cl.
CPC ... *G01N 33/004* (2013.01); *G01N 2021/3155* (2013.01); *G01N 2021/3166* (2013.01); *G01N 2201/061* (2013.01)

(58) Field of Classification Search
USPC .................................................. 356/432–440
See application file for complete search history.

(56) References Cited

U.S. PATENT DOCUMENTS

| | | | |
|---|---|---|---|
| 6,067,840 A * | 5/2000 | Chelvayohan | G01N 21/3504 250/343 |
| 8,269,972 B2 * | 9/2012 | Cole | G01N 21/3504 356/437 |
| 2005/0173635 A1 | 8/2005 | Smith | |
| 2009/0009769 A1 * | 1/2009 | Uber | G01N 21/1702 356/437 |
| 2011/0228803 A1 * | 9/2011 | Guenter | H01L 21/2654 372/38.07 |

* cited by examiner

CO2 CONCENTRATION SENSOR

CROSS-REFERENCE TO RELATED APPLICATION

This Application is a 35 USC §371 US National Stage filing of International Application No. PCT/FR2013/053281 filed on Dec. 30, 2013, and claims priority under the Paris Convention to French Patent Application No. 13 50014 filed on Jan. 2, 2013.

FIELD OF THE DISCLOSURE

The present invention relates to devices for measuring the concentration of a predetermined gas, in particular CO2.

BACKGROUND OF THE DISCLOSURE

More particularly, the invention relates to a device for measuring the concentration of a predetermined gas, comprising a cavity holding the predetermined gas in a concentration to be measured, a light source capable of emitting light rays within the cavity, particularly infrared rays, and an infrared detector configured to receive a portion of the infrared rays within a predetermined spectral range corresponding to high absorption of the predetermined gas.

It is known from prior art document U.S. Pat. No. 8,003,944 to place a second infrared detector in order to create a reference channel which allows eliminating the slow drifts related to aging of the lamp for example. The detectors in question are expensive and bulky. In addition, their power consumption is a disadvantage.

There is therefore a need to optimize this kind of device to reduce the cost and size, but without diminishing their performance and accuracy.

SUMMARY OF THE DISCLOSURE

To this end, the invention proposes a device for measuring the concentration of a predetermined gas, in particular CO2, comprising:

a cavity holding a gas mixture containing the predetermined gas in a concentration to be measured, a light source capable of emitting, within the cavity, light rays within a basic spectral range including visible and infrared, a photosensitive detector, configured to receive a portion of the light rays within a first predefined spectral range corresponding to high absorption of the predetermined gas, and to convert a received power into an electrical signal, a photodiode configured to receive a portion of the light rays within a second predetermined spectral range corresponding to low absorption of the predetermined gas, a control unit configured to calculate the concentration of the predetermined gas by comparing an electrical signal representative of the radiant power received by the detector to an electrical signal representative of the radiant power received by the photodiode, wherein the photodiode operates in the visible range, meaning $\lambda 2$ between 0.4 and 0.8 µm.

With these arrangements only one detector is used, a thermopile detector, and there is still a reference channel that enables eliminating from the calculation the rapid or slow drifts of the device such as defects due to aging or newness of the light source, the presence of condensation in the cavity, fouling of the cavity, etc.

In addition, an inexpensive photodiode is used, making the CO2 sensor attractive in price.

In embodiments of the device according to the invention, one or more of the following arrangements may be used alone or in combination:

the predetermined gas may be carbon dioxide CO2 and the gas mixture ambient air; enabling measurement of the CO2 concentration in ambient air;

the device may comprise a filter interposed between the source and the detector, said filter being centered on the wavelength $\lambda 1=4.26$ µm; thus primarily measuring the attenuation caused by CO2 while eliminating other attenuation phenomena;

the cavity may have a generally tubular shape, preferably with a diameter less than 10 mm and a length preferably less than 10 cm, the rays being directed substantially in an axial direction X of the tubular shape; whereby such a device can be integrated into an object of relatively moderate dimensions;

the photodiode may be arranged in a radial position relative to the axial direction X of the tubular shape; so that the dimensions can be further reduced and mechanical integration facilitated;

the cavity may be an aluminum tube or a plastic tube coated with a metal deposit on its inner surface; this provides a cavity that is both easy to manufacture and provides good optical reflectance coefficients on its inner surface;

there is no filter interposed between the light source and the photodiode; so that the second measurement channel (reference channel) is particularly simple and does not require adjustment or adaptation;

the light source is a filament lamp or a light emitting diode (LED), preferably controlled by an intermittent control; whereby an inexpensive light source is used and the average power consumption is reduced;

the type of detector may be thermopile or pyroelectric or a photodiode operating in the infrared range; advantageously a single detector of this type is used so that the cost of the sensor is reduced;

the cumulative power consumption of the detector and photodiode is less than 1 mA when they are activated for a measurement; enabling such a sensor to be embedded in a standalone device having relatively moderate autonomy in terms of electrical energy.

Other features and advantages of the invention will be apparent from the following description of one of its embodiments, given by way of non-limiting example with reference to the accompanying drawings.

DETAILED DESCRIPTION OF THE DISCLOSURE

In the various figures, the same references designate identical or similar elements.

Figure 1:
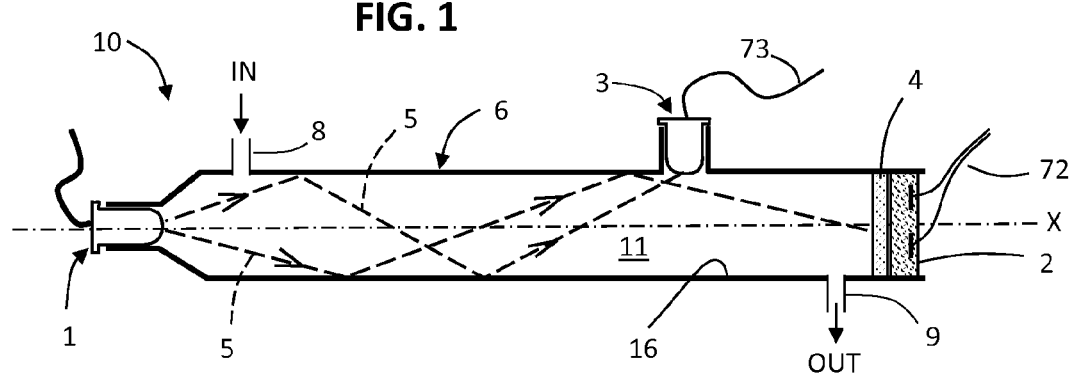
FIG. 1 is a schematic view of the device for measuring the concentration of a gas according to the invention.

FIG. 1 shows a device 10 for measuring the concentration of a predetermined gas, which in the current example is the carbon dioxide (CO2) present in ambient air.

However, the principle presented allows using such a device to measure the concentration of any predetermined gas having light absorption properties, particularly light rays in the infrared range, said predetermined gas being comprised in a given gas mixture 11.

The device firstly comprises a cavity 6 which holds the gas mixture 11 containing the predetermined gas in a concentration to be measured; in the example shown, the gas mixture is the ambient air that enters the cavity through an inlet 8 denoted 'IN' and that exits through an outlet 9 denoted 'OUT'; however, there could be only one opening acting as both inlet and outlet. In the example illustrated, the cavity takes the form of a straight tube; the shape could be very different, however, with the generatrix of the tube being curved; the cavity could also be in the form of a torus or any other geometric arrangement. The casing of the cavity may be made of aluminum or of plastic coated with a metal deposit on its inner surface.

In addition, the device 10 comprises a light source 1, more generally a source of electromagnetic radiation including visible light rays and infrared rays, which are emitted into the cavity. In the present description, the term 'light source' or 'light rays' is therefore not limited to the visible range.

The light source 1 may be a conventional filament lamp. Alternatively, a light emitting diode (LED) may be used.

The light source emits light rays 5 within a reference spectral range including the visible (0.4 to 0.8 µm) and infrared (0.8 µm to 500 µm).

The light rays 5 are reflected on the inner surface 16 of the cavity and are captured by various entities which will be detailed below.

Figure 4:
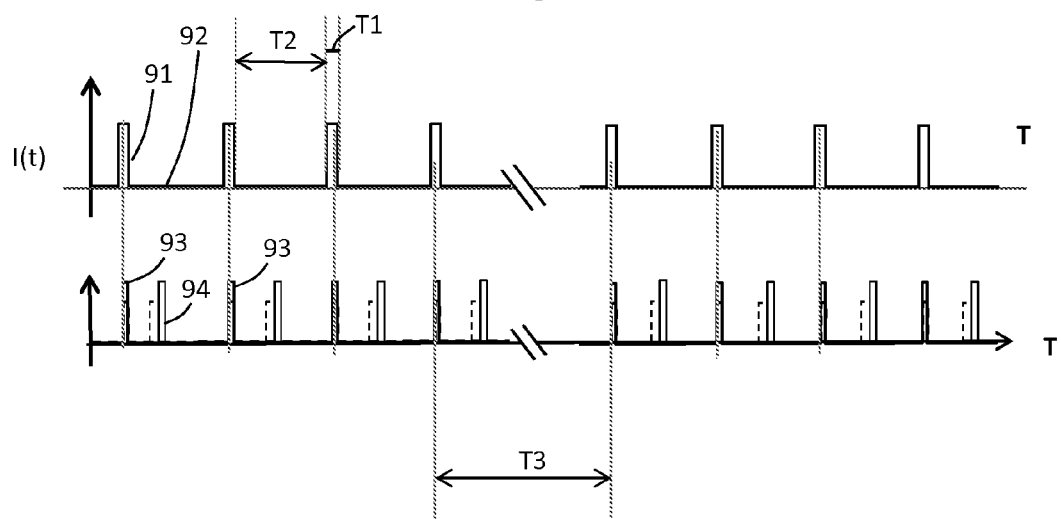
FIG. 4 shows timing diagrams relating to the device of FIG. 1.

In addition, the lamp 1 is preferably controlled by an intermittent control as shown in FIG. 4 which will be discussed below.

In addition, the device 10 comprises a detector 2, which receives a portion of the light rays 5 within a first predefined spectral range corresponding to high absorption of the predetermined gas. This detector provides an electrical signal proportional to the power of the light received by the detector, which forms part of what can also be called a first measurement channel of the CO2 sensor.

The detector may be a thermopile detector (such as the Dexter S60M TO-5 detector) or pyroelectric (such as the the Infratec LIE-201). Alternatively, a photodiode detector operating in the infrared can be used.

Advantageously, a filter 4 may be placed upstream of the detector, so that the filter is interposed between the light source 1 and the detector 2. In this case, the power of the light received is restricted to the portion of the spectrum passing through the filter, illustrated by the spectral characteristic denoted 21 in FIG. 2A.

Figure 2A:
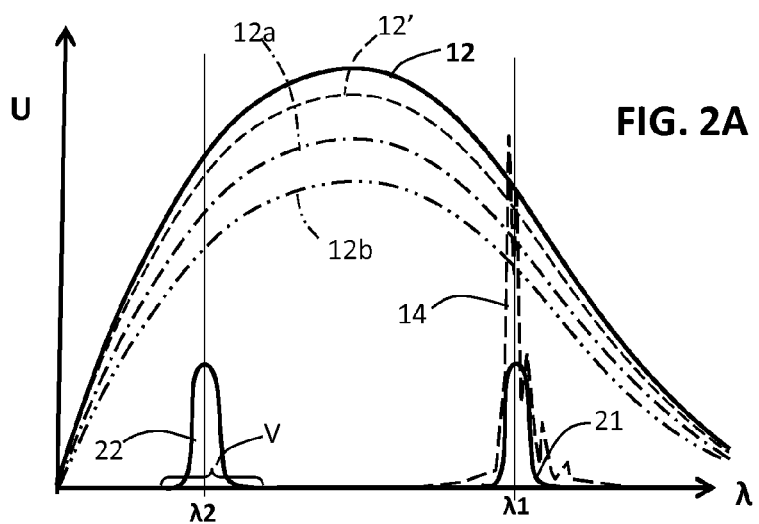
FIGS. 2A and 2B show spectral diagrams of the device of FIG. 1.

Referring to FIG. 2A, the light source 1 emits electromagnetic radiation within a spectral range including the infrared and the visible light range V; more specifically, this emission is characterized by a power spectral density curve 12 which indicates the wavelength distribution of all the radiation emitted by the light source 1. In the case of a filament lamp, this spectral density is more the wide band type as shown, while for an LED, the spectral density curve will be narrower while encompassing the visible range V and at least a portion of the near infrared range.

The lamp emission characteristics change over time; an increase in the power emitted or a reduction in the power emitted or both phenomena, one after the other, may be observed. The aging of the lamp 1 causes a change in the power emitted, which is illustrated by curve 12a, which could be reduced as shown (it could also be increased). This is not the only factor which impacts the power received by the detector 2. In fact, deposits of condensation, dust, or impurities on the inner surface of the cavity alter the reflectance of the light rays 5 and consequently reduce the power reaching the detector 2, which is illustrated by the curve denoted 12b.

It is therefore necessary to take into account these changes, which can be referred to as 'drifts' (slow or fast), so that the CO2 concentration calculation is free of errors related to these drifts.

Variations in the initial characteristics of the light sources must also be taken into account: for example, a different lamp will present a different power spectral density curve 12'.

The device 10 therefore comprises a photodiode 3 configured to receive a portion of the light rays within a second predefined spectral range corresponding to low absorption of the predetermined gas (CO2 here), constituting a second measurement channel. It should be noted that the light rays are received directly by the photodiode 3, with no filter interposed between the source 1 and the photodiode.

More specifically, the photodiode 3 is primarily sensitive to wavelengths in the visible range (0.4 to 0.8 µm); this can also be illustrated by the bandpass-type spectral characteristic denoted 22 centered on $\lambda 2$. CO2 absorbs almost no visible light radiation and therefore the amount of light received by the photodiode 3 is not dependent on the concentration of CO2 in the cavity. The amount of light or luminous power received by the photodiode 3 is, however, dependent on the power emitted by the lamp 1 and on the reflectance coefficients of the inner walls 16 of the cavity.

It should be noted that this type of photodiode sensitive to visible radiation is very inexpensive because it mainly uses a silicon core.

The attenuation of the rays that is characteristic of CO2 is illustrated according to wavelength by the dotted curve denoted 14 in FIG. 2A. Advantageously, the filter 4 is a bandpass filter centered on $\lambda 1$, which coincides with the maximum attenuation region of the curve 14. For CO2, the wavelength $\lambda 1$ is selected so that $\lambda 1 = 4.26$ µm (microns).

Figure 2B:
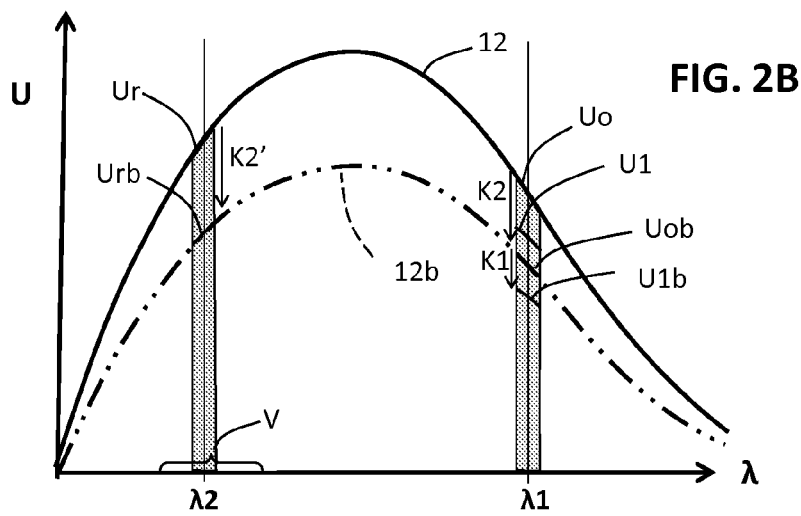

Referring to FIG. 2B, the power received by the photodiode 3 (second channel) is represented by the reference quantity Ur when the measurement device is in new condition, the quantity Ur being known from testing after manufacture of the CO2 sensor; over time and due to modifications that may occur, the reference quantity Ur becomes Urb, which takes into account not only the lamp's decrease in power but also all drifts that may occur concerning the lamp and the cavity.

Advantageously according to the invention, the amounts of light measured on the first and second channels are in fact determined by the difference between an active state in which the lamp is on and a rest state in which the lamp is off. Specifically, for all values U or $U_x$ expressed in the previous paragraph or the following paragraphs, we are to understand that $U = U_{ON} - U_{OFF}$. This eliminates any continuous component due to ambient light or light noise.

As to the first measurement channel for the detector 2, the amount of light received by the detector 2, which corresponds to a CO2 concentration of zero, is denoted Uo; the amount of light received for a CO2 concentration to be measured is denoted U1, which is lower than Uo due to attenuation.

With the effects of aging, represented by curve 12b, the amount of light received by the detector 2, which corresponds to a CO2 concentration of zero, is denoted Uob; the amount of light received for the CO2 concentration to be measured is denoted U1b, which is lower than Uob due to attenuation.

U1b/Uob=U1/Uo is the attenuation factor K1 on channel λ1, due to the attenuating effect of CO2.

In addition, Uob/Uo and Urb/Ur are drift factors related to aging and other phenomena as mentioned above; they are respectively denoted K2 and K2'. They are related by a predetermined function F, for example K2'=F(K2).

$$K1 = \frac{U1b}{Uob} = \frac{U1b}{Uo} \cdot G(Urb/Ur), \quad \text{(Equation 1)}$$

where function G combines the correction factors, particularly those related to K2 and K2'.

In a simplified version, function F can be approximated by the identity function and a simplified expression of the above equation can thus be obtained:

$$K1 = \frac{U1b}{Uob} = \frac{U1b \cdot Ur}{Uob \cdot Urb} \quad \text{(Equation 1a)}$$

Where necessary, corrections are also added for the temperature and ambient pressure (see below).

Knowing that Uo and Ur are known from the initial calibration of the sensor, and that Urb and U1b correspond to the luminous power measurements (ON/OFF differential to eliminate a continuous component, ambient light) measured at the detector 2 and the photodiode 3, Equation 1 is used to determine the attenuation factor associated with the presence of CO2. Next one refers to an abacus-type chart that relates the attenuation factor to the CO2 concentration. This abacus-type chart may also take into consideration the ambient temperature and pressure.

To be able to implement the above operations, the device 10 comprises a control unit 7 supplied by a power source 18 such as a conventional or rechargeable battery.

Figure 3:
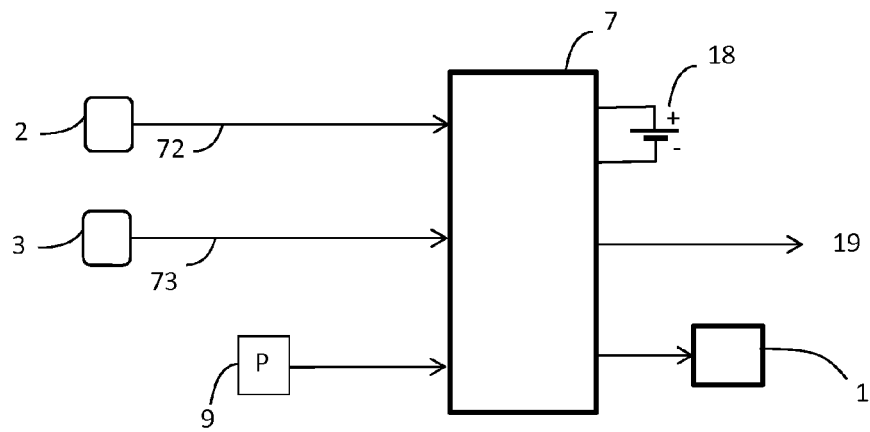
FIG. 3 shows a schematic wiring diagram of the device of FIG. 1.

Referring to FIG. 3, the detector 2 is connected to the control unit by an electrical connection 72, and the photodiode 3 is connected to the control unit by an electrical connection 73.

In addition, a pressure sensor 9 and a temperature sensor may be provided so that the control unit 7 can acquire information concerning the ambient atmospheric pressure and ambient temperature. Furthermore, the temperature sensor (not shown) may be embedded in the board of the control unit 7.

Referring to FIG. 4, the control unit 7 controls the light source 1 in a predetermined sequence.

Specifically, in the example shown, the lamp is set to the ON state 91 for a time T1 of 200 ms, then is set to the OFF state 92 for a time T2 of 600 ms. This sequence is repeated four times in the example shown, but the number of repetitions can be arbitrary.

The corresponding measurements 93,94 of luminous power received are obtained with each repetition, during period T1 in the ON state ($U_{ON}$ as already mentioned above, denoted 93) and also during period T2 in the OFF state ($U_{OFF}$ as already mentioned above, denoted 94). As already indicated, it is the difference in power between the ON and OFF state that is used when calculating the amount of light received by both the detector 2 and the photodiode 3.

The measurement sequence is repeated after a period of inactivity of predetermined duration T3; this period may be selected from a range of values between 10 minutes and 30 minutes. The average consumption of the CO2 sensor is therefore very low.

It should be noted that the power consumption of the photodiode is about 10 μA (microamps); in fact it is much lower than the power consumption of a thermopile sensor which consumes slightly less than 1 mA. The combined power consumption of the detector and the photodiode is therefore less than 1 mA when activated for measurement.

In addition, data transmission may advantageously be provided via a wireless link 19 to a user system.

After the initial assembly of the sensor, a calibration step is carried out in which the characteristic of the lamp's power spectral density curve is determined. For example, the quantity Ur can be measured. One can also measure the quantity U1 for a known CO2 concentration, and thus find the quantity Uo used in Equation 1 above.

Advantageously, such a compact and inexpensive CO2 concentration sensor can be integrated into certain objects of common use, such as a digital bathroom scale, a personal activity monitor, etc.

The invention claimed is:

1. A device for measuring the concentration of a predetermined gas comprising at least CO2, comprising:
   a cavity holding a gas mixture containing the predetermined gas in a concentration to be measured,
   a light source capable of emitting, within the cavity, light rays within a basic spectral range including visible and infrared,
   a detector configured to receive a portion of the light rays within a first predefined spectral range corresponding to high absorption of the predetermined gas,
   a photodiode configured to receive a portion of the same light rays within a second predetermined spectral range corresponding to low absorption of the predetermined gas,
   a control unit configured to calculate the concentration of the predetermined gas by comparing electrical signals respectively representative of the radiant power received by the detector and of the radiant power received by the photodiode, wherein the photodiode operates in the visible range, meaning λ2 between 0.4 and 0.8 μm.

2. The device according to claim 1, wherein the predetermined gas is carbon dioxide CO2 and the gas mixture is ambient air.

3. The device according to claim 2, comprising a filter interposed between the source and the detector, said filter being centered on the wavelength λ1=4.26 μm.

4. The device according to claim 1, wherein the cavity has a generally tubular shape with a diameter less than 10 mm and a length less than 10 cm, the rays being directed substantially in an axial direction (X) of the tubular shape.

5. The device according to claim 4, wherein the photodiode is arranged in a radial position relative to the axial direction (X) of the tubular shape.

6. The device according to claim 4, wherein the cavity is an aluminum tube or a plastic tube coated with a metal deposit on its inner surface.

7. The device according to claim 1, wherein there is no filter interposed between the light source and the photodiode.

8. The device according to claim 1, wherein the light source is a filament lamp or a light emitting diode LED controlled by an intermittent control.

9. The device according to claim 1, wherein the type of detector is thermopile or pyroelectric or a photodiode operating in the infrared range.

10. The device according to claim 9, comprising a single detector of said type.

11. The device according to claim 1, wherein the cumulative power consumption of the detector and photodiode is less than 1 mA when they are activated for a measurement.

* * * * *